United States Patent [19]

Ujvári et al.

[11] Patent Number: 4,745,128
[45] Date of Patent: May 17, 1988

[54] NOVEL CARBAMIC ACID ESTER DERIVATIVES, PESTICIDAL COMPOSITIONS CONTAINING THEM AND A PROCESS FOR THEIR PREPARATION

[75] Inventors: István Ujvári; György Matolcsy; Iván Bélai; László Varjas; Béla Darvas, all of Budapest, Hungary

[73] Assignee: Innofinance Altalanos Innovacios Penzintezet, Budapest, Hungary

[21] Appl. No.: 1,835

[22] Filed: Jan. 9, 1987

[51] Int. Cl.$^4$ .................. C07C 145/04; A01N 47/12
[52] U.S. Cl. ................................ 514/483; 560/13; 560/16
[58] Field of Search ............... 560/13, 16; 514/483

[56] References Cited

U.S. PATENT DOCUMENTS

| | | | |
|---|---|---|---|
| 3,531,523 | 9/1970 | Nelson | 564/79 |
| 3,709,677 | 1/1973 | Houlihan | 564/79 |
| 4,298,617 | 11/1981 | Fahmy | 564/101 |
| 4,382,957 | 5/1983 | D'Silva | 564/101 |

*Primary Examiner*—Michael L. Shippen
*Attorney, Agent, or Firm*—Keil & Weinkauf

[57] ABSTRACT

The present invention relates to pesticides containing carbamic acid ester derivatives of the formula (I),

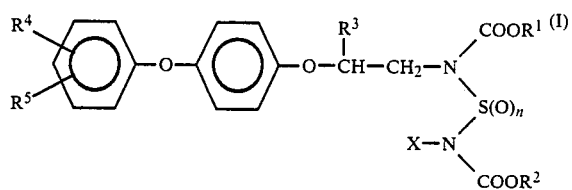

to pesticide compositions containing these compounds and to a process for their preparation.

In the general formula
$R^1$ is alkyl of from one to four carbon atoms;
$R^2$ represents alkyl of from one to four carbon atoms or (when X is alkyl of from one to twelve carbon atoms) alkyl of from one to twelve carbon atoms;
$R^3$ is H, methyl or ethyl;
$R^4$ and $R^5$ are, independently from each other, H or halogen atoms;
$n=0$, 1 or 2;
X represents alkyl of from one to twelve carbon atoms or an 4-aryloxyphenoxyalkyl group of formula (II).

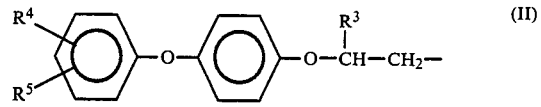

The pesticide of the invention can be used for controlling insects and mites.

6 Claims, No Drawings

NOVEL CARBAMIC ACID ESTER DERIVATIVES, PESTICIDAL COMPOSITIONS CONTAINING THEM AND A PROCESS FOR THEIR PREPARATION

The present invention relates to N-sulfenyl-carbamic acid esters, N-sulfinyl-carbamic acid esters and N-sulfonyl-carbamic acid esters of the formula (I),

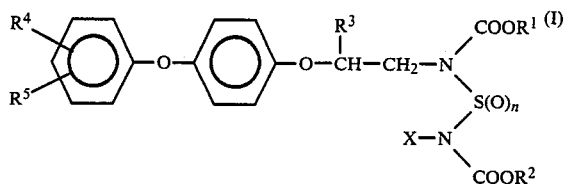

to processes for their preparation, to their use in pest control, especially as insecticides and acaricides, and pesticidal compositions.

The compounds having the general formula (I), wherein
$R^1$ is alkyl of from one to four carbon atoms;
$R^2$ represents alkyl of from one to four carbon atoms or (when X is alkyl of from one to twelve carbon atoms) alkyl of from one to twelve carbon atoms;
$R^3$ is H, methyl or ethyl;
$R^4$ and $R^5$ are, independently from each other, H or halogen, preferably Cl, Br or F atoms;
n=0, 1 or 2;
X represents alkyl of from one to twelve carbon atoms or an 4-aryloxyphenoxyalkyl group of formula (II),

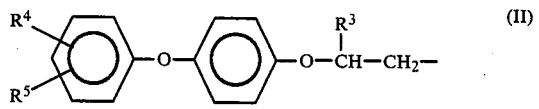

where $R^3$, $R^4$ and $R^5$ are as above.

If X stands for the group of formula (II), then $R^3$, $R^4$ and $R^5$ correspond to the groups $R^3$, $R^4$, and $R^5$ in formula (I).

If X represents alkyl of from one to twelve carbon atoms, it is preferably alkyl of from one to eight carbon atoms. Examples of such groups are methyl, ethyl, n-propyl, isopropyl, n-butyl, n-octyl and the like.

If $R^2$ represents alkyl of from one to twelve carbon atoms, examples of such groups are methyl, ethyl, n-propyl, isopropyl, n-butyl, n-octyl, n-dodecyl and the like.

The alkyl groups defined above may have straight or branched chain.

U.S. Pat. No. 4,215,139 and European Pat. No. 4334 disclose insecticidal compositions containing 2-phenoxyethylcarbamates of formula (A),

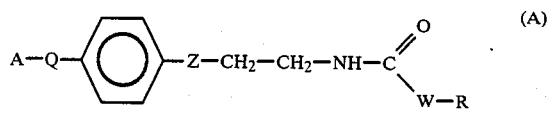

wherein, inter alia, A is substituted phenyl, Z is oxygen, sulfur atom or methylene group, W is oxygen or sulfur, R is alkyl of from one to six carbon atoms, and Q is oxygen atom, sulfur atom, sulfonyl, carbonyl or methylene group.

Published European patent application No. 138,037 describes pesticidal carbamates of formula (B),

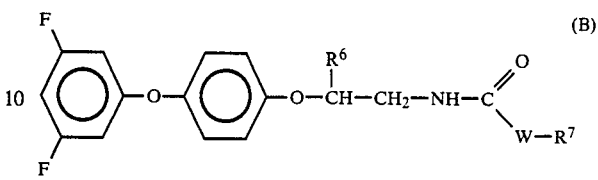

wherein $R^6$ is H or methyl, W is oxygen or sulfur, and $R^7$ is alkyl group.

U.S. Pat. No. 4,413,010 discloses insecticidal carbamates of formula (C),

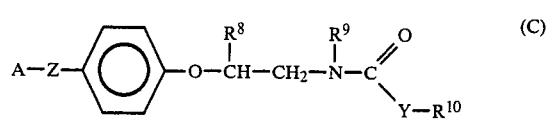

wherein A is substituted phenyl, Z is oxygen, sulfur atom or methylene group, $R^8$ is H or methyl, $R^9$ is H or alkyl group containing one to four carbon atoms, Y is oxygen or sulfur and $R^{10}$ is alkyl containing one to four carbon atoms.

Published German patent application (DOS) No. 3,334,983 discloses insecticidal N-aryl-sulfenyl-carbamate derivatives of formula (D),

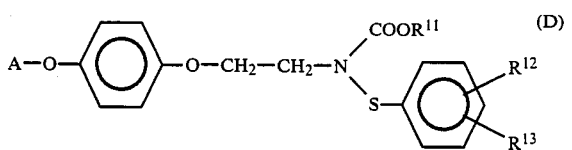

wherein A is substituted phenyl, $R^{11}$ is alkyl or alkoxy group containing one to six carbon atoms, $R^{12}$ and $R^{13}$ are H, halogen nitro, trifluoromethyl or lower alkyl.

The present invention is directed to develop novel pesticidal agents which are more efficient than the presently used ones and are not harmful to non-target organisms, especially vertebrates.

Now we have found that pesticidal compositions containing compounds described by the general formula (I) as the active ingredient influence the hormonal regulating system of the morphogenesis of insects and mites and inhibit metamorphosis causing death or abnormalities at later developmental stages. The presently used insecticides exert their killing effect by acting on the nervous system.

We have also found that compounds of formula (I) are active at very low doses, have longer duration of activity but they are not persistent in the field. They are also selective and non-toxic to vertebrates.

The invention is also directed to processes for the preparation of the compounds of formula (I).

The compounds of formula (I) can be prepared by methods (a) or (b) as shown on Schemes [A] and [B].

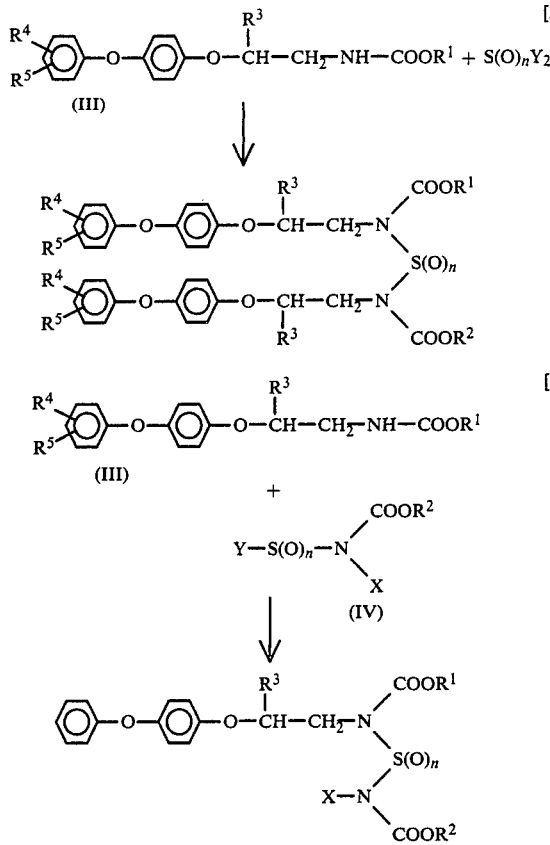

(a) Carbamate derivatives of formula (I), where X stands for a group (II), $R^1$, $R^2$, $R^3$, $R^4$, $R^5$ and n are as defined above, are prepared by reacting a carbamic acid derivative of formula (III) with a sulfur compound of the general formula $S(O)_nY_2$, wherein Y is halogen, preferably Cl or Br and n is 0, 1 or 2.

The reaction is carried out in an inert, aprotic organic solvent, preferably diethyl ether, tetrahydrofuran, acetone, halogenated hydrocarbons or pyridine, or a mixture of these solvents. The use of an acid acceptor is advantageous. Sulfur dichloride, sulfur monochloride, thionyl chloride and sulfuryl chloride can be used as sulfur compound. The reaction temperature can range from $-10°$ C. to the boiling point of the solvent. As acid acceptor, the usual inorganic or organic bases can be used. These are alkali metal carbonates (e.g. $K_2CO_3$), alkali metal hydrides (e.g. NaH), or tertiary amines containing one or two nitrogen atoms, such as triethylamine, pyridine, 4-dimethylaminopyridine, 1,4-diazabicyclo[2.2.2]octane or a mixture thereof. Pyridine can also be used as solvent. The molar ratio of carbamate (III), the sulfur compound and the acid acceptor is preferably 2:1–1.2:1.9–50. The reaction product is separated from the reaction mixture by known procedures, e.g. by extraction.

(b) For the preparation of compounds (I), where X is an alkyl group containing one to twelve carbon atoms and the other substituents have the same meaning as reported earlier, the carbamate of formula (III) is reacted with a carbamate derivative of formula (IV), where Y and n are as above. The reaction is carried out in an inert solvent and in the presence of an acid acceptor as described in Method (a), at a temperature ranging from $-10°$ C. to the boiling point of the solvent.

The molar ratio of compounds (III), (IV) and the acid acceptor is preferably 1:1–2:0.9–20.

Compounds of formula (IV) can be preferably prepared "in situ", immediately before the reaction described above, from the corresponding carbamic acid ester and a sulfur compound of formula $S(O)_nY_2$, where n is as defined above.

The reaction product is isolated by known procedures, for example by extraction.

The starting materials for the preparation of compounds of formula (I) are known or can be prepared by known methods. For example, 2-(4-phenoxyphenoxy)ethylcarbamic acid esters of formula (III) can be prepared as described in U.S. Pat. No. 4,215,139 or European Pat. No. 4334. N-chlorosulfinylcarbamic acid esters of formula (IV) can be prepared as described by Fahmy et al. (J. Agric. Food Chem. 26, 550 /1978/).

Compounds of formula (I) where n is 1 or 2 can be prepared by the oxidation of compounds of formula (I) where n is 0. The oxidation is accomplished by known methods using oxidizing agents, for example 1–5 molar equivalents—depending on the desired product—of organic peracids. The reaction is carried out in an inert organic solvent.

The invention is illustrated by the following non-limiting Examples. The structure of the compounds was proven by their elemental analyses, IR and NMR spectra.

EXAMPLE 1

Ethyl N,N'-sulfenyl-bis[2-(4-phenoxyphenoxy)-ethylcarbamate]

(Compound No. 1)

To an ice-cooled solution of 3.2 g (0.01 mole) of ethyl 2-(4-phenoxyphenoxy)-ethylcarbamate, 0.9 ml of dry pyridine and 0.36 g of 4-dimethylaminopyridine in 20 ml of dry dichloromethane 0.35 ml (0.0055 mole) of sulfur dichloride is added, and the solution is stirred at ambient temperature for 18 hours. The mixture is diluted with 30 ml of chloroform, washed with 20 ml each of 5% hydrochloric acid solution, saturated sodium hydroxide carbonate solution and water, dried, and concentrated in vacuo. The residue is purified by column chromatography to give 0.77 g of a light yellowish viscous oil. The compound is characterized by the physical constants shown in Table 1.

The following compounds were prepared in an analogous manner:

Isopropyl N,N'-sulfenyl-bis(2-/4-phenoxyphenoxy/-ethylcarbamate) (Compound No. 2) (oil);

Propyl N,N'-sulfenyl-bis[2-(4-/3-fluorophenoxy/-phenoxy)-ethylcarbamate] (Compound No. 3) (oil);

(±) Ethyl N,N'-sulfenyl-bis[2-(4-/2,4-dichlorophenoxy/-phenoxy)-propylcarbamate] (Compound No. 4) (oil);

Ethyl N,N'-sulfenyl-bis[2-(4-/4-chlorophenoxy/-phenoxy)-ethylcarbamate] (Compound No. 5) (oil);

Ethyl N,N'-sulfenyl-bis[2-(4-/3,5-dichlorophenoxy/-phenoxy)-ethylcarbamate] (Compound No. 6) (oil).

EXAMPLE 2

Ethyl N,N'-sulfinyl-bis(2-/4-phenoxyphenoxy/-ethylcarbamate) (Compound No. 7)

To an ice-cooled solution of 2.0 g (0.0066 mole) of ethyl 2-(4-phenoxyphenoxy)-ethylcarbamate, 1.1 ml (0.008 mole) of triethylamine in 6 ml of dry tetrahydrofurane 0.25 ml (0.0034 mole) of thionyl chloride is added and the solution is stirred at 30° C. for 18 hours. 10 ml of benzene and 10 ml of hexane are added, the mixture is washed with 10 ml each of dilute hydrochloric acid, saturated sodium hydrogen carbonate solution and water, dried, and concentrated in vacuo. The residue is purified by column chromatography to give 0.68 g of a light viscous oil. The physical characteristics of the compounds are given in Table 1.

The following compounds were prepared in an analogous manner:

Isopropyl N,N'-sulfinyl-bis[2-(4-phenoxyphenoxy)-ethylcarbamate] (Compound No. 8) (oil);

(±) Ethyl N,N'-sulfinyl-bis[2-(4-/2,4-dichlorophenoxy/-phenoxy)-propylcarbamate] (Compound No. 9) (oil);

Ethyl N,N'-sulfinyl-bis[2-(4-/4-chlorophenoxy/-phenoxy)-ethylcarbamate] (Compound No. 13) (oil).

EXAMPLE 3

[N-/(Ethoxycarbonyl-isopropylamino)sulfenyl]-2-(4-phenoxyphenoxy)-ethylcarbamic acid ethyl ester (Compound No. 10)

To an ice-cooled solution of 2.0 g (0.0066 mole) of 2-(4-phenoxyphenoxy)ethylcarbamate and 5 ml of dry pyridine 1.3 g (0.0067 mole) of ethyl N-(chlorosulfenyl)-isopropylcarbamate is added and the solution is stirred at ambient temperature for 18 hours. The reaction mixture is diluted with 20 ml of diethyl ether and 20 ml of hexane, the precipitate is filtered, the filtrate is washed successively with 20 ml each of dilute hydrochloric acid, saturated sodium hydrogen carbonate solution and water, dried, and concentrated in vacuo. The residue is purified by column chromatography to give 1.8 g of a light viscous oil. The physical characteristics of the compounds are given in Table 1.

The following compounds were prepared in a analogous manner:

[N-(n-Octyloxycarbonyl-methylamino)sulfenyl]-2-(4-phenoxyphenoxy)-ethylcarbamic acid ethyl ester (Compound No. 11) (oil);

[N-(n-Dodecyloxycarbonyl-butylamino)sulfenyl]-2-(4-phenoxyphenoxy)-ethylcarbamic acid ethyl ester (Compound No. 12) (oil).

TABLE 1

Physical constants of compounds of formula (I)

| Compound No. | S content calc. % | S content found % | N content calc. % | N content found % | Cl content calc. % | Cl content found % | IR cm |
|---|---|---|---|---|---|---|---|
| 1 | 5.07 | 5.19 | 4.43 | 4.33 | | | 1711 (C = O) |
| 2 | 4.60 | 5.03 | 4.02 | 3.82 | | | 1715 (C = O) |
| 3 | 4.50 | 4.61 | 3.93 | 3.87 | | | 1710 (C = O) |
| 4 | 4.02 | 4.15 | 3.51 | 3.45 | 8.88 | 8.93 | 1715 (C = O) |
| 5 | 4.57 | 4.80 | 3.99 | 3.90 | 10.11 | 10.00 | 1715 (C = O) |
| 6 | 4.02 | 4.16 | 3.51 | 3.46 | 8.88 | 8.94 | 1715 |
| 7 | 4.94 | 5.02 | 4.32 | 4.28 | | | (C = O) 1717 (C = O) 1298 (S = O) |
| 8 | 4.74 | 4.80 | 4.14 | 4.11 | | | 1710 (C = O) |
| 9 | 4.07 | 4.21 | 3.56 | 3.18 | 18.03 | 17.62 | 1719 (C = O) 1297 (S = O) |
| 10 | 6.93 | 6.68 | 6.06 | 5.78 | | | 1709 (C = O) |
| 13 | 4.47 | 4.60 | 3.90 | 3.86 | 9.88 | 9.75 | 1715 (C = O) 1296 (S = O) |

The carbamate derivatives of general formula (I) have pesticidal activity; thus they can be used as active ingredients of insecticidal and acaricidal compositions.

The biological activity of the compounds has been tested in laboratory as well as in the field.

EXAMPLE 4

Laboratory experiments with *Pieris brassicae*

The morphogenetic activity of the compounds was tested on 24-hour old last instar caterpillars of the large cabbage white, *Pieris brassicae*, collected from a constant laboratory culture. The compounds to be assayed were topically applied to the dorsal surface of thorax using doses ranging from 0.01 to 0.1 μg/specimen in 2 μl of acetone solution, each dose to 25 to 50 larvae. The treated groups of 12 to 15 caterpillars were kept in plastic cups of 0.5 liter at 25° C. and 18 hours/day exposure to light, continuously fed with fresh cabbage leaves. The percentages of morphogenetically affected forms—or larvae incapable of living—as well as normal pupae were estimated after the the moult or pupation of insects.

The results arre shown in Table 2.

TABLE 2

| Compound No. | Dosis mg/caterpillar | Morphogenetically suffered caterpillars % |
|---|---|---|
| 1 | 0.1 | 100 |
| | 0.01 | 100 |
| 7 | 0.1 | 100 |
| | 0.01 | 90 |
| 10 | 0.1 | 100 |
| | 0.01 | 89 |

EXAMPLE 5

Field test on fall webworm (*Hyphantria cunea*)

The following composition in the form of a wettable powder was prepared from a compound of formula (I) as an active ingredient, where $R^1 = R^2$ is ethyl, $R^3$ is H, and X is 2-(4-phenoxyphenyl)-ethyl, n=0 (Compound No. 1):

active ingredient—50%
kaolin—40%
sodium lignosulfonate
sodium lauryl sulfate

All percentages refer to mass based on the total mass of the composition.

From this concentrate, suspensions containing 0.01, 0.001 and 0.0001% by volume of the active ingredient were prepared by appropriate dilution with water. These suspensions were sprayed onto branches of plum (Prunus) tree in special isolator. These branches had been previously infested with 50—50 last instar ($L_7$-stage) larvae of the fall webworm, Hyphantria cunea. An assessment was made after 20 days. The results showed that all treatments caused a complete or substantial (up to 90%) reduction of viable pupae, as compared to an untreated control experiment where no morphogenetical abnormalities could be observed and 100% of the larvae emerged as moth.

EXAMPLE 6

Laboratory experiments with *Quadraspidiotus perniciosus*

8 ml of an acetonic solution of 5 millimoles of the compounds of formula (I) (see Table 3) was sprayed onto a fruit of *Cucurbita ficifolia*. Then the fruit was infected with 50–60 larvae of the San José scale (*Quadraspidiotus perniciosus*) reared on non-treated *Cucurbita ficifolia*. The experiment was conducted at 28° C. An evaluation was made three months after the treatment and the efficacy of the treatment was expressed in percentages using the Henderson-Tilton formula. The results are shown in Table 3.

TABLE 3

| Compound No. | Efficacy % |
|---|---|
| Control | 0 |
| 1 | 100 |
| 5 | 78 |
| 7 | 100 |
| 10 | 100 |
| 11 | 100 |
| 12 | 100 |
| 13 | 0 |

For application, the compounds of formula (I) can be processed into the form of dust, emulsion concentrates, granulates, water-dispersible concentrates, solutions, using usual auxiliary materials.

The content of the active ingredient in the composition is between 0.0001 and 95% by mass, preferably 0.01 to 80% by mass.

The composition can contain, as auxiliary materials, solid or liquid carriers, diluting or excipient materials as well as surface active agents. The solid or liquid auxiliary materials can be natural or artificial origin, and are known in common practice and described in the literature.

The surface active agents can be ionic or non-ionic dispersing agents, emulsifier or wetting agents, etc.

Depending on the application, the composition can contain other commonly used auxiliary materials, antioxidants, stabilizers, odorant substances, etc.

The pesticidal composition of the invention can be used in agriculture against insects and mites and also in other, especially sanitary, areas where the presence of insects and mites is harmful.

The insecticidal properties of the compounds of the invention can be improved by so-called synergizing agents which enhance their activity. Examples of synergists are piperonyl butoxide, propargyl ether derivatives and S,S,S-tributyl-trithiophosphate.

The following examples illustrate the composition of an emulsion concentrate:

| (A) active ingredient | 40 parts by weight |
|---|---|
| N—methyl-pyrrolidone | 50 parts by weight |
| polyethylene glycol | 10 parts by weight |
| (B) active ingredient | 25 parts by weight |
| xylene | 55 parts by weight |
| dimethyl sulfoxide | 10 parts by weight |
| triethanolamine | 5 parts by weight |
| cationic tenside | 5 parts by weight |

What we claim is:

1. An insecticidal and arachicidal composition comprising carbamic acid ester derivatives as active ingredients of the formula (I)

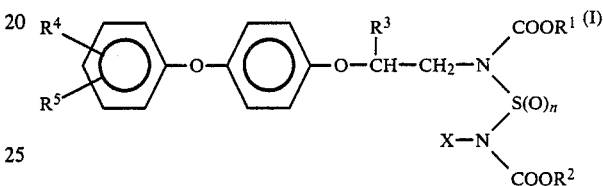

wherein
$R^1$ is alkyl of from one to four carbon atoms;
$R^2$ represents alkyl of from one to four carbon atoms or (when X is alkyl of from one to twelve carbon atoms) alkyl of from one to twelve carbon atoms;
$R^3$ is H, methyl or ethyl;
$R^4$ and $R^5$ are, independently from each other, H or halogen, preferably Cl, Br or F atoms;
n=0, 1 or 2;
X represents alkyl of from one to twelve carbon atoms or a 4-aryloxyphenoxyalkyl group of formula (II)

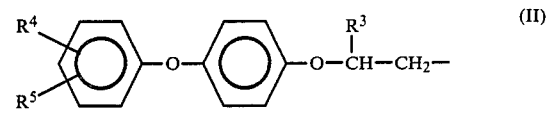

where $R^3$, $R^4$ and $R^5$ are as defined above—together with inert carrier(s).

2. An insecticidal and arachicidal composition as claimed in claim 1, wherein the active ingredient content is between 0.0001 and 95% by mass.

3. An insecticidal and arachicidal composition as claimed in claim 1, wherein the active ingredient is ethyl N,N'-sulfenyl-bis[2-(4-phenoxyphenoxy)ethylcarbamate] or ethyl N,N'-sulfenyl-bis[2-(4-/3,5-dichlorophenoxy/-phenoxy)-ethylcarbamate] or ethyl N,N'-sulfinyl-bis(2-/4-phenoxyphenoxy/-ethylcarbamate) or N-[(ethoxycarbonyl-isopropylamino)-sulfenyl]-2-(4-phenoxyphenoxy)-ethylcarbamic acid ethyl ester or [N-(n-octyloxycarbonyl-methylamino)-sulfenyl]-2-(4-phenoxyphenoxy)-ethylcarbamic acid ethyl ester or [N-(n-dodecyloxycarbonyl-butylamino)-sulfenyl]-2-(4-phenoxyphenoxy)-ethylcarbamic acid ethyl ester.

4. Carbamic acid ester derivatives of the formula (I),

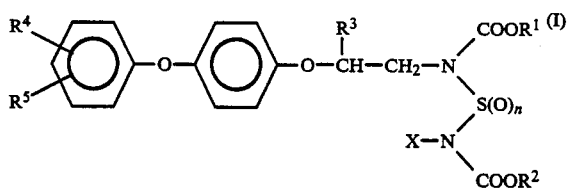

wherein
- $R^1$ is alkyl of from one to four carbon atoms;
- $R^2$ represents alkyl of from one to four carbon atoms or (when X is alkyl of from one to twelve carbon atoms) alkyl of from one to twelve carbon atoms;
- $R^3$ is H, methyl or ethyl;
- $R^4$ and $R^5$ are, independently from each other, H or halogen, preferably Cl, Br or F atoms;
- n=0, 1 or 2;

X represents alkyl of from one to twelve carbon atoms or a 4-aryloxyphenoxyalkyl group of formula (II)

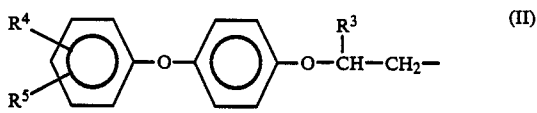

where $R^3$, $R^4$ and $R^5$ are as above.

5. A method for controlling insects and arachnids, which comprises applying to the insects or arachnids or to the area to be protected, an effective amount of the composition as defined in claim 1.

6. A method as defined in claim 5 wherein an effective amount of a composition as defined in claim 3 is used to control insects and arachnids.

* * * * *